US 11,717,338 B2
(12) United States Patent
Garcia-Bengochea et al.

(10) Patent No.: US 11,717,338 B2
(45) Date of Patent: Aug. 8, 2023

(54) BIPOLAR DISSECTOR

(71) Applicant: JGMG BENGOCHEA, LLC, Jacksonville, FL (US)

(72) Inventors: Javier Garcia-Bengochea, Jacksonville, FL (US); John Souza, Monroe, NC (US)

(73) Assignee: JGMG BENGOCHEA, LLC, Jacksonville, FL (US)

( * ) Notice: Subject to any disclaimer, the term of this patent is extended or adjusted under 35 U.S.C. 154(b) by 639 days.

(21) Appl. No.: 16/566,419

(22) Filed: Sep. 10, 2019

(65) Prior Publication Data
US 2020/0078086 A1 Mar. 12, 2020

Related U.S. Application Data

(60) Provisional application No. 62/729,306, filed on Sep. 10, 2018.

(51) Int. Cl.
*A61B 18/00* (2006.01)
*A61B 18/12* (2006.01)
*A61B 18/14* (2006.01)

(52) U.S. Cl.
CPC .. *A61B 18/1445* (2013.01); *A61B 2018/0091* (2013.01); *A61B 2018/00339* (2013.01);
(Continued)

(58) Field of Classification Search
CPC ...... A61B 18/1445; A61B 2018/00446; A61B 2018/00339; A61B 2018/0091;
(Continued)

(56) References Cited

U.S. PATENT DOCUMENTS 5,527,313 A * 6/1996 Scott ................. A61B 18/1442
606/41
5,989,249 A * 11/1999 Kirwan, Jr. ............ A61B 18/14
606/41
(Continued)

OTHER PUBLICATIONS

Sharma S, Haji AG, Vijaykumar DK, Shaji AK. Irrigation-coupled bipolar cautery unit: A practical, economical, and simple version. Indian J Plast Surg. Jul. 2008;41(2):162-6. doi: 10.4103/0970-0358. 44932. PMID: 19753257; PMCID: PMC2740501. (Year: 2008).*
(Continued)

*Primary Examiner* — Daniel W Fowler
*Assistant Examiner* — Annie L Shoulders
(74) *Attorney, Agent, or Firm* — McNees Wallace & Nurick LLC

(57) ABSTRACT

A bipolar dissector includes a handle actuatable by squeezing, a housing extending from and coupled to a distal end of the handle, and a shaft coupled to a proximal end of the handle and extending past the distal end of the handle and through the housing to a distal end of the housing. The shaft includes first and second electrical lines extending from a proximal end to a distal end of the shaft and an insulating material electrically insulating the electrical lines from each other and from the handle and the housing. The bipolar dissector also includes a pair of forceps including a first tine and a second tine. The tines extend from the electrical lines at the distal end of the shaft at the distal end of the housing. Squeezing the handle actuates the forceps in the same direction as the squeezing.

20 Claims, 8 Drawing Sheets

(52) U.S. Cl.
CPC ............ *A61B 2018/00446* (2013.01); *A61B 2018/00565* (2013.01); *A61B 2018/126* (2013.01); *A61B 2218/002* (2013.01); *A61B 2218/007* (2013.01)

(58) Field of Classification Search
CPC .... A61B 2018/00565; A61B 2218/007; A61B 2218/002
See application file for complete search history.

(56) References Cited

U.S. PATENT DOCUMENTS

| | | | |
|---|---|---|---|
| 7,879,033 B2 | 2/2011 | Sartor et al. | |
| 9,023,035 B2 | 5/2015 | Allen et al. | |
| 9,539,049 B2 | 1/2017 | Allen et al. | |
| 2006/0036237 A1* | 2/2006 | Davison | A61B 18/1482 606/49 |
| 2007/0106297 A1* | 5/2007 | Dumbauld | A61B 18/085 606/171 |
| 2015/0148801 A1* | 5/2015 | Shahlaie | A61B 18/1445 606/51 |
| 2017/0007317 A1 | 1/2017 | Allen et al. | |
| 2017/0231686 A1* | 8/2017 | Sartor | A61B 18/149 606/46 |
| 2017/0325886 A1* | 11/2017 | Graham | A61B 18/1482 |
| 2018/0085157 A1* | 3/2018 | Batchelor | A61B 18/1445 |
| 2018/0310984 A1* | 11/2018 | Kallenberger | A61B 18/1445 |
| 2018/0368910 A1* | 12/2018 | Kirwan, Jr. | A61B 18/1442 |
| 2019/0126442 A1* | 5/2019 | Batchelor | A61B 18/1445 |

OTHER PUBLICATIONS

AVM Micro Clip System, Brochure, Aesculap, Inc., p. 1-6, 2016, Center Valley, PA, USA www.aesculapusa.com.
KLS Martin Non-Stick red diatermipinsett, accessed Sep. 4, 2019, https:www.dma.no.produkter/kls-martin-non-stick-red-diatermipinsett-429/.
Bissinger, "Bipolar Micro-Coagulation Forceps," Mithras brochure, p. 1-3, product CE0297.
Stingray Surgical Products, "Ultralite Disposable Bipolar Forceps," https://stingraysurgical.com/home/products/disposable-bipolar-forceps/, accessed Mar. 9, 2021.
Indiamart "Bipolar Forceps Bayonet", ID No. 16481067297, https://www.indiamart.com/proddetail/bipolar-forceps-bayonet-16481067297.html, accessed Mar. 9, 2021.
Elliquence, "Bipolar Forceps," https://www.elliquence.com/products/bipolar-forceps/, accessed Mar. 9, 2021.
"Codman 80-1125 Surgical Bayonet Bipolar Titanium Forceps," https://www.ebay.com/p/Codman-Titanium-Bipolar-Bayonet-Forceps-80-1125/1101822344, accessed Mar. 9, 2021.
Ambler Surgical, "Snyder-Osher IOL removal forceps, curved shaft," Item #G-32997, https://amblersurgical.com/g-32997-snyder-osher-iol-removal-forceps-curved-shaft-0-7mm-diameter-straight-serrated-grasping-tips-flat-squeeze-handle, accessed Mar. 29, 2021.

* cited by examiner

FIG. 5
FIG. 6
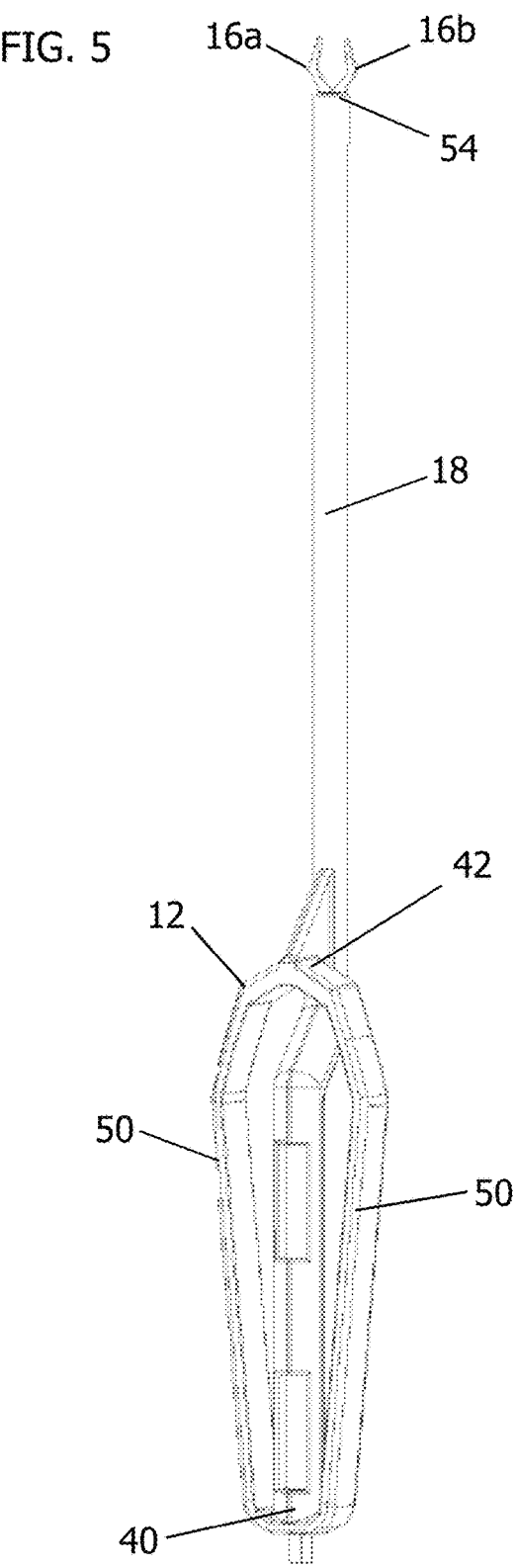
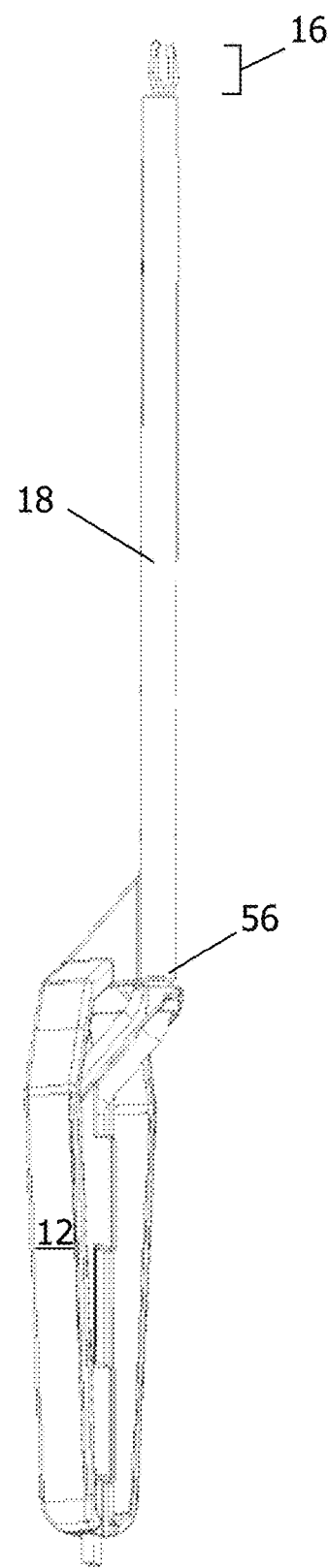

BIPOLAR DISSECTOR

CROSS-REFERENCE TO RELATED APPLICATIONS

This application claims priority to and the benefit of U.S. Provisional Application No. 62/729,306 filed Sep. 10, 2018, which is hereby incorporated by reference in their entirety.

FIELD

The present embodiments are directed to electrosurgical instruments. More particularly, the present embodiments are directed toward a bipolar dissector.

BACKGROUND

Electrosurgical forceps, typically referred to as bipolars or bipolar dissectors, provide the dual utility of mechanical manipulation of materials and tissue and application of a bipolar electrical current to provide for purposes of cutting, coagulating, dissecting, or fulgurating tissue. Such devices are well known in the art, and typically include either opposing tweezer-like extensions and a compressible tweezer-like handle or elongate extensions with tweezer-like or scissor-like pincers that are connected with and actuated by a pistol-type grip. The various commercial devices include elongate electrosurgical members that emit an electrical current at their opposing/cooperative distal tips. The electrical current is typically a radio-frequency alternating current. The electrosurgical members are controlled by a surgeon by actuation of the handle. The tweezer-type devices are generally lightweight and disposable. The pistol grip devices may be disposable or reusable.

A failing of current devices is the lack of a clamping grip action that can be actuated under the control of a tweezer-like action. Due to the space constraints and fine detail of many surgical procedures, use of an elongate pistol-activated device presents serious limitations for most surgeons, and introduces maneuverability, control, and precision problems. These problems may adversely affect the efficiency of the surgical procedure, creating undesirable delays and imprecision in the execution of the surgical manipulation of the tissue. There is a need for adaptations to such surgical instrumentation to provide precision and control together with functionalities that include one or more of suction and irrigation-type fluidic management in the device that integrates electrosurgical features.

BRIEF DESCRIPTION

In an embodiment, a bipolar dissector includes a handle actuatable by squeezing, a housing extending from and coupled to a distal end of the handle, and a shaft coupled to a proximal end of the handle and extending past the distal end of the handle and through the housing to a distal end of the housing. The shaft includes a first electrical line extending from a proximal end of the shaft to a distal end of the shaft, a second electrical line extending from a proximal end of the shaft to a distal end of the shaft, and an insulating material electrically insulating the first electrical line and the second electrical line from each other and from the handle and the housing. The bipolar dissector also includes a pair of forceps including a first tine and a second tine. The first tine extends from the first electrical line at the distal end of the shaft at the distal end of the housing and the second tine extends from the second electrical line at the distal end of the shaft at the distal end of the housing. Squeezing the handle actuates the forceps in the same direction as the squeezing.

In some embodiments, the handle is offset from an axis of the housing.

In some embodiments, electrical leads are electrically coupled to the first electrical line and the second electrical line at the proximal end of the shaft and couplable to an electricity source.

In some embodiments, the shaft further includes a fluid channel extending from a proximal end of the shaft to the distal end of the shaft.

In some embodiments, the handle includes a pair of arms elastically squeezable to actuate the forceps.

In some embodiments, the distal end of the housing extends axially toward the forceps upon actuation of the handle and pushes on the forceps to cause distal tips of the forceps toward each other.

In some embodiments, the distal tips of the forceps are straight and splayed in a retracted state.

In some embodiments, the distal tips of the forceps are straight and parallel to each other in a retracted state.

In some embodiments, the first tine and the second tine each include a curved surface contacted by the housing upon actuation of the handle.

In some embodiments, the first tine and the second tine each include a flat surface contacted by the housing upon actuation of the handle.

In some embodiments, the housing is cylindrical.

In some embodiments, an axis of the housing is curved in a plane of the forceps.

In some embodiments, an axis of the housing is curved in a plane perpendicular to a plane of the handle.

In some embodiments, the housing is not straight in extending from the handle.

In another embodiment, a method of electrosurgery includes placing a pair of forceps of a bipolar dissector at an electrosurgical site. The bipolar dissector includes a handle, a housing extending from and coupled to a distal end of the handle, a shaft coupled to a proximal end of the handle and extending past the distal end of the handle and through the housing to a distal end of the housing, and the pair of forceps, including a first tine and a second tine. The shaft includes a first electrical line extending from a proximal end of the shaft to a distal end of the shaft, a second electrical line extending from a proximal end of the shaft to a distal end of the shaft, and an insulating material electrically insulating the first electrical line and the second electrical line from each other and from the handle and the housing. The first tine extends from the first electrical line at the distal end of the shaft at the distal end of the housing and the second tine extending from the second electrical line at the distal end of the shaft at the distal end of the housing. The method also includes squeezing the handle to actuate the forceps. Squeezing the handle actuates the forceps in the same direction as the squeezing.

In some embodiments, the method further includes applying suction to the electrosurgical site by way of a fluid channel through the shaft of the bipolar dissector.

In some embodiments, the method further includes providing irrigation to the electrosurgical site by way of a fluid channel through the shaft of the bipolar dissector.

In some embodiments, the squeezing further includes grabbing and pulling tissue at the electrosurgical site with the forceps.

In some embodiments, the method further includes supplying an electrical current to the forces by way of the first electrical line and the second electrical line.

Other features and advantages of the present invention will be apparent from the following more detailed description, taken in conjunction with the accompanying drawings which illustrate, by way of example, the principles of the invention.

BRIEF DESCRIPTION OF THE DRAWINGS

FIG. 5 is an elevated side view of the bipolar dissector of FIG. 1.

FIG. 6 is a lowered side view of the bipolar dissector of FIG. 1.

Wherever possible, the same reference numbers will be used throughout the drawings to represent the same parts.

DETAILED DESCRIPTION

Provided is a surgical instrument for use in a wide variety of roles that may include, but are not limited to, grasping, dissecting, clamping, and/or retracting materials or tissue during surgical procedures performed in topical surgery, such as, for example, cosmetic surgery; in open surgery, such as, for example, brain surgery; or in surgery within the abdominal cavity.

Embodiments of the present disclosure, for example, in comparison to concepts failing to include one or more of the features disclosed herein, provide a squeezing force sufficient to grab and pull tissue in a bipolar instrument, provide actuation by squeezing of a handle in the same direction as the squeezing of the forceps in a bipolar instrument, provide irrigation in a bipolar instrument, provide suction in a bipolar instrument, and/or combinations thereof.

Figure 1:
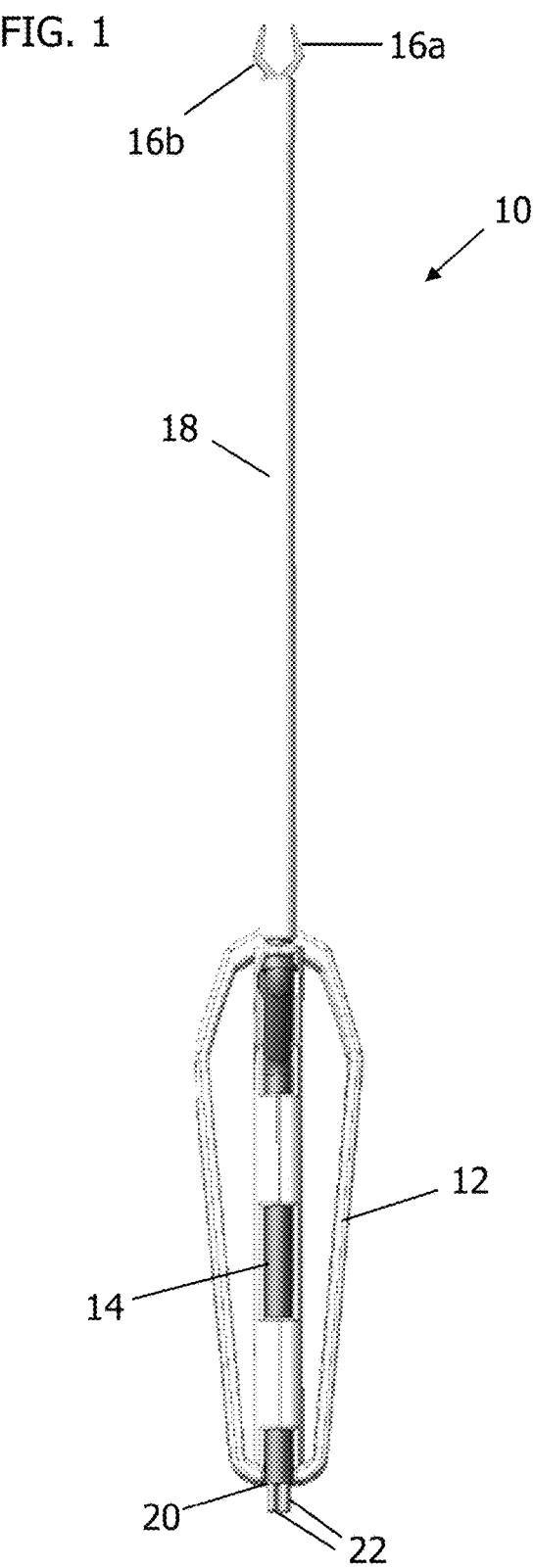
FIG. 1 is a bottom view of a bipolar dissector in a retracted state in an embodiment of the present disclosure.

Referring to FIG. 1, the bipolar dissector 10 includes a handle 12, a shaft 14 coupled to and extending from the handle 12, a pair of forceps 16 extending from the shaft 14 on the end opposite the handle 12, and a housing 18 coupled to the handle 12 and extending around the shaft 14. The pair of forceps 16 includes a first tine 16a and a second tine 16b. The proximal end 20 of the shaft 14 includes electrical leads 22 that are electrically connected with the forceps 16. The center of the shaft 14 along its length lies within a plane perpendicular to the plane of the view of FIG. 1. The bipolar dissector 10 is shown in a retracted state in FIG. 1 through FIG. 6.

Figure 2:
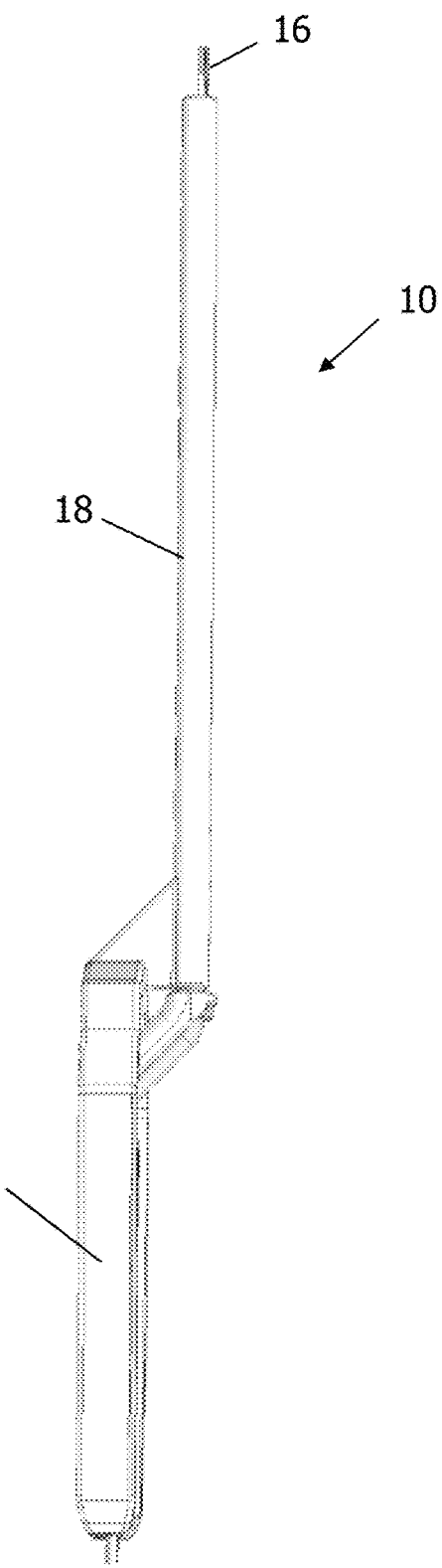
FIG. 2 is a side view of the bipolar dissector of FIG. 1

Referring to FIG. 2, the handle 12 of the bipolar dissector 10 is offset from the axis of the housing 18. More specifically, the handle 12 lies in a plane substantially parallel to, but offset from, the plane in which the forceps 16 and the axis of the housing 18 lie. The shaft 14 also follows the offset of the handle 12 from the housing 18, extending through both the handle 12 and the housing 18. As shown in FIG. 1 and FIG. 2, the housing 12 is cylindrical in shape.

Figure 3:
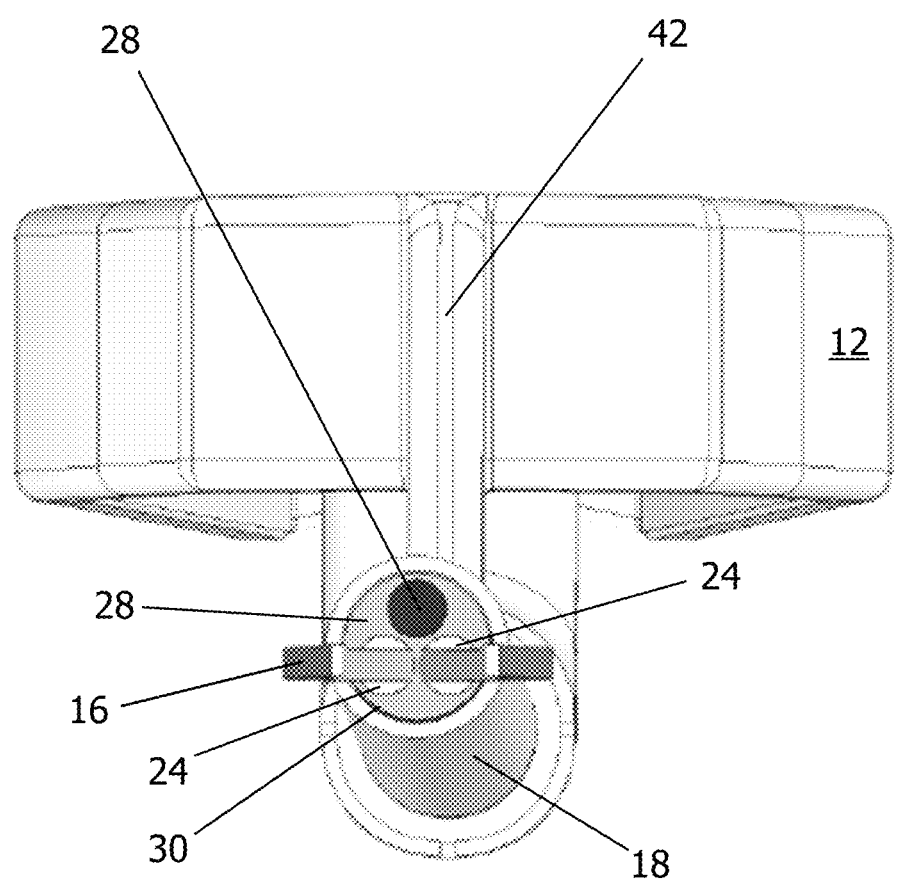
FIG. 3 is an end view of the bipolar dissector of FIG. 1.

Referring to FIG. 3, the shaft 14 includes electrical lines 24 that separately conduct electricity from each of the two electrical leads 22 to each of the two forceps 16. In some embodiments, each of the two forceps 16 is integral with its respective electrical line 24. The shaft 14 also includes insulating material 26 that electrically insulates the electrical lines 24 from each other and from the handle 12 and the housing 18. The shaft 14 may optionally contain a fluid channel 28 that fluidly connects the opposite ends of the shaft 14 and is also electrically insulated from the electrical lines 24. The forceps 16 extend from the distal end 30 of the shaft 14.

Figure 4:
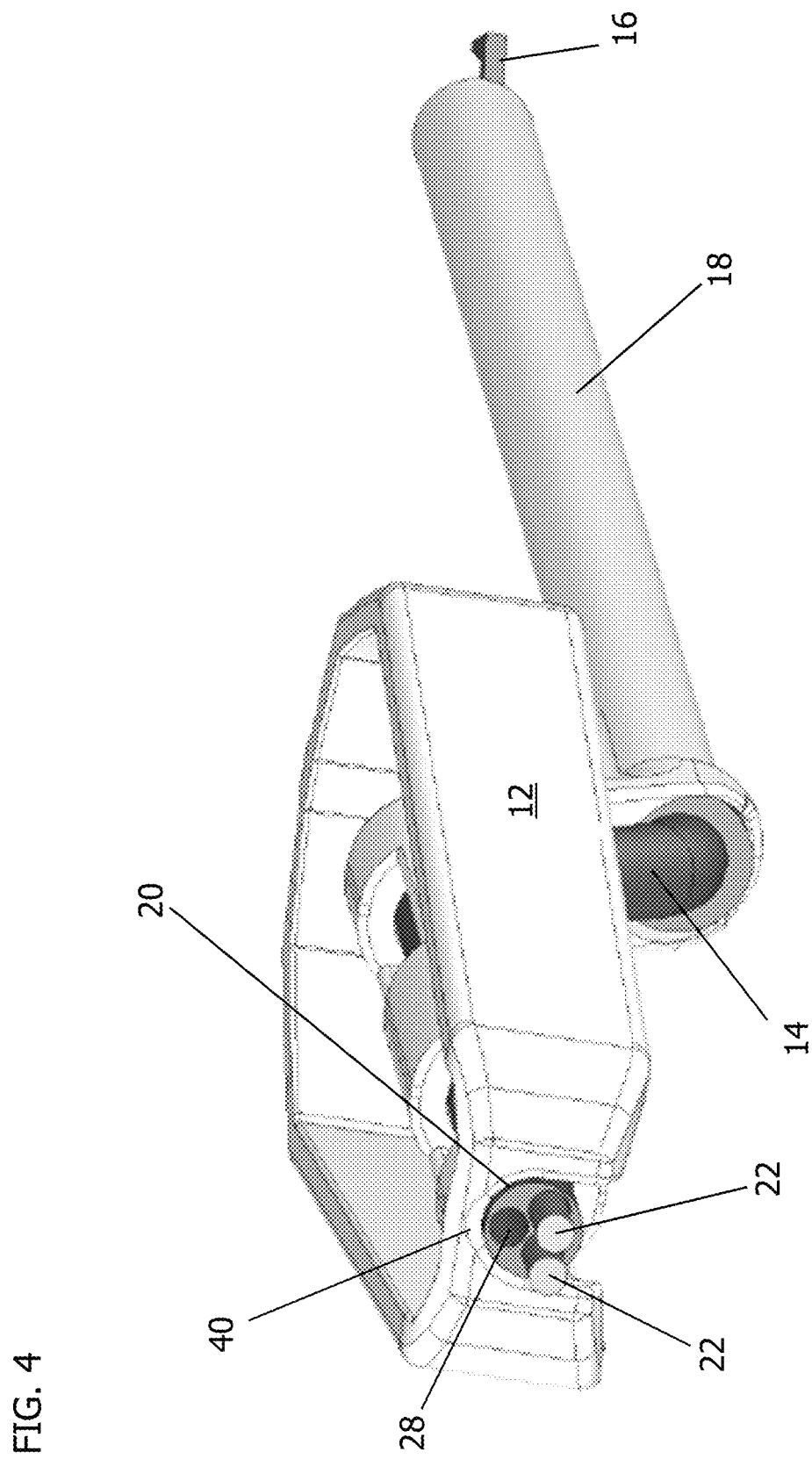
FIG. 4 is an elevated perspective rear view of the bipolar dissector of FIG. 1.

Referring to FIG. 4, the electrical leads 22 are each separately connectable to an appropriate electrical source (not shown), and the fluid channel 28 is connectable to tubing (not shown) at the proximal end 40 of the handle 12 for either providing suction to remove fluid from the surgical site or providing irrigation to apply fluid to the surgical site.

Figure 7:
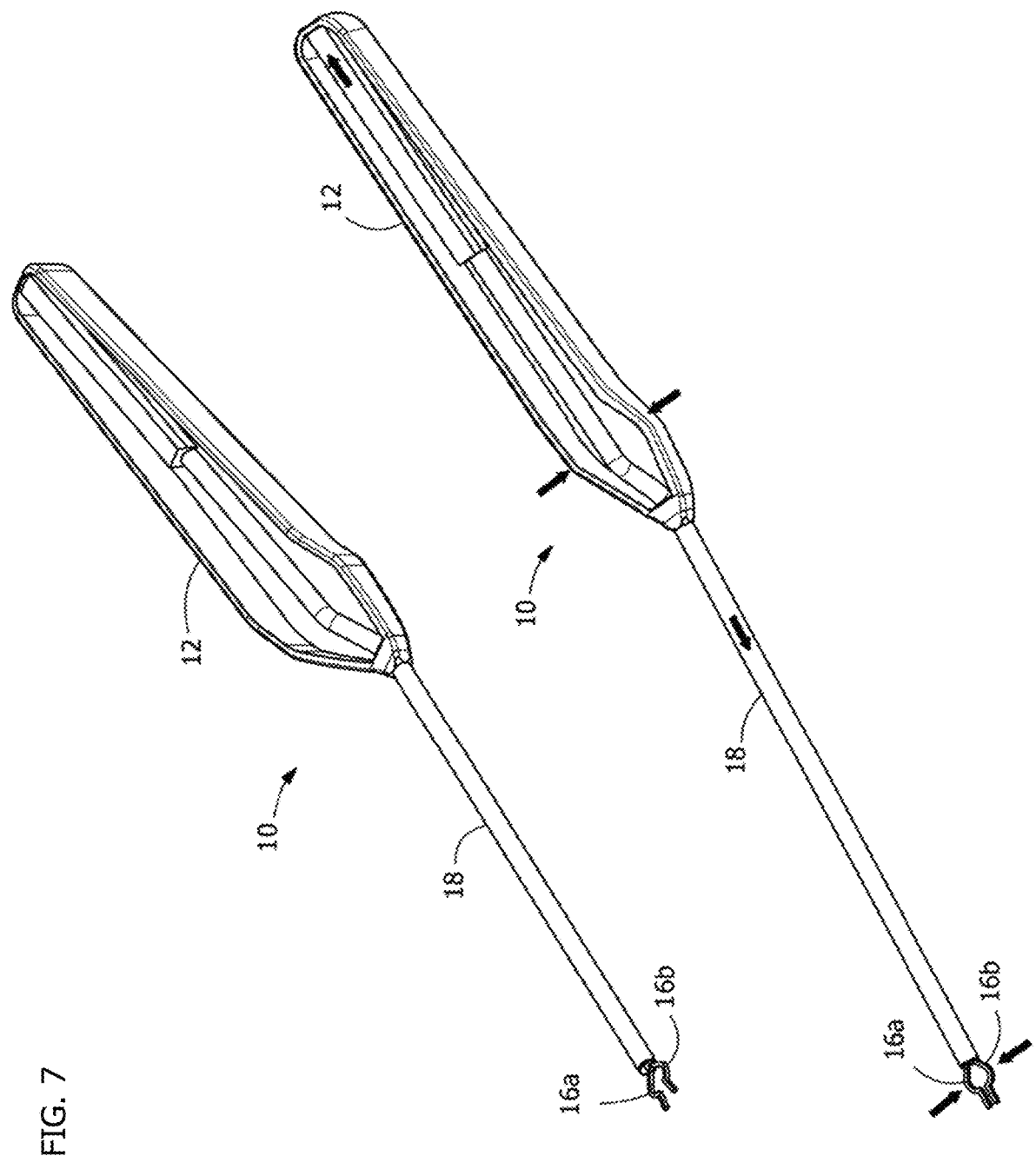
FIG. 7 is an elevated side view of a process of gripping with the bipolar dissector of FIG. 1.

Referring to FIG. 5, FIG. 6, and FIG. 7, actuation of the handle 12 by squeezing the arms 50 of the handle toward the shaft 14, such as by a hand of the user of the bipolar dissector 10, causes the handle 12 to elastically deform. Being fixed to the shaft 14 at the proximal end 40, the handle 12 elastically deforms to extend at the distal end 42 toward the forceps 16, thereby pushing the housing 18 axially with respect to the shaft 14 toward the forceps 16. The distal end 54 of the housing 18 extends to press on the outer surfaces of the angled proximal ends of the forceps 16, causing the forceps 16 to come toward each other and eventually together at their distal tips in a pinching movement. FIG. 7 shows the bipolar dissector 10 in the retracted state and in the closed or unretracted state.

As shown in FIG. 7, the squeezing force is applied in the same direction as the direction of the closing of the forceps 16. This gives the user a feeling of the squeezing force being connected to the closing action of the forceps 16. The handle 12, the housing 18, and/or the forceps 16 may be biased toward the retracted state by one or more springs (not shown), such as, for example, leaf springs. The housing 18 may be integral with, or otherwise coupled to, the distal end 42 of the handle 12. The housing 18 is not coupled to the shaft 14. Removal of the squeezing force causes the handle 12, the housing 18, and the forceps 16 to elastically return to the retracted state.

In some embodiments, the surgical instrument includes a handle 12 formed of opposing compressible arms 50 that are attached at opposing ends to form a generally elongated elliptical shape, as shown in FIG. 5. In other embodiments, the shape of the handle 12 may be more rounded or may be squared. The instrument includes, attached to the handle 12, a shaft 14 with a generally circular cross section that extends from proximal to distal ends of the instrument, passing through the handle 12 and extending beyond the distal end of the handle 12 to terminate at a distal end of the housing 18 for contact with and manipulation of tissue. The shaft 14 is covered by a solid housing 18 along at least a portion of its length and contains an extension member that terminates at the distal end in opposing grasping blades or tines 16*a*/16*b* as a pair of forceps 16. The cylindrical shaft 14 also contains one or more of suction and irrigation channels 28, which may include separate channels for each, an electrical lead 22 for delivering electrical current at the forceps 16, and an insulating material 26 to maintain separation between the irrigation channels 28 and the electrical lines 24. Of course, in some embodiments, the shaft 14 may lack the irrigation port features and may thus include only insulating material 26 and electrical lines 24.

In use, the handle 12 is grasped and squeezed to direct movement of the tubular housing 18 along a linear path in a direction from the proximal end 56 toward the distal end 54 so as to extend toward and over the tines 16*a*/16*b* and thereby compress them. Squeezing the handle 12 actuates the forceps 16 in the same direction as the squeezing direction. Release of compression on the handle 12 causes the housing 18 to retract towards the proximal end 56, thereby exposing more of the tines 16*a*/16*b* and effectively releasing them from compressed contact. Adjustable compression of the tines 16*a*/16*b* enables the user to control the gripping and release of tissue between the forceps 16. Controllers and actuators (not shown) connected to the irrigation channel 28 and electrical lines 24 enable controlled acutation of those features. The controller/actuator may be located remotely from the bipolar dissector 10, such as, for example, in the form of one or more foot petals actuated by a foot of the user to start or stop flow of electrical current, flow of irrigation fluid, and/or application of suction. The bipolar dissector 10 may be formed of various materials. In some embodiments, the handle 12 and tubular housing 18 may be formed of plastic, and at least the forceps 16 may be formed of metal at their distal ands and may be attached to opposing arms that are formed of metal or plastic. The shaft 14 within the housing 18 may be formed of plastic, and such plastic may include insulative material.

The bipolar dissector 10 may have any appropriate dimensions. In some embodiments, the housing 18 is about 15 cm in length. In some embodiments, a cross section of the cylindrical shaft 14 has a diameter of about 3.5 mm, although the shaft 14 may have any appropriate cross sectional shape, such as, for example, elliptical, oval, square, rectangular, or polyhedral. In some embodiments, the forceps have a length of about 15 mm and a thickness of about 5 mm.

In some embodiments, the forceps 16 are metal with no insulating cover. In other embodiments, at least a portion of the forceps 16, starting from the proximal end, is covered with an electrical insulation, such as, for example, to prevent metal-metal contact between the housing 18 and the forceps 16 during actuation, but the distal tips are not. More generally, when any portion of the housing 18 is made of an electrically-conductive metal or another electrically-conductive material, the contact surfaces for contact between the housing 18 and the forceps 16 during actuation include one surface being non-electrically conductive to prevent electrical current from flowing into the housing 18.

Referring to FIG. 8, FIG. 9, FIG. 10*a*, and FIG. 10*b*, the forceps 16 may have any appropriate shape complementary to the housing 18 such that axial extension of the housing 18 applies a force to surfaces of the forceps 16 sufficient to bring the distal tips of the tines 16*a*/16*b* into contact with each other. Appropriate shapes include tines 16*a*/16*b* that angle away from the axis of the housing 18 farther than the radial length of the housing 18 from the proximal end of the tines 16*a*/16*b* toward a mid-portion of the tines 16*a*/16*b* with the tines 16*a*/16*b* angling toward each other and toward the axis of the housing 18 at or toward the distal tips.

Figure 8:
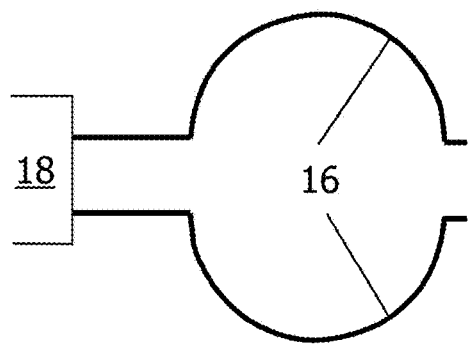
FIG. 8 shows forceps of a bipolar dissector with curved tines in an embodiment of the present disclosure.
Figure 9:
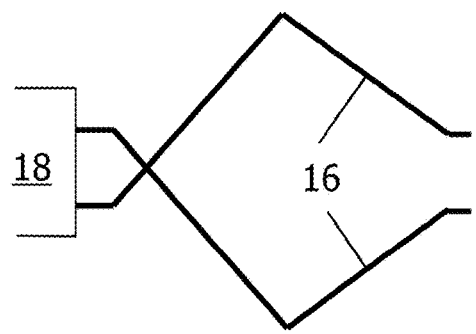
FIG. 9 shows forceps of a bipolar dissector with flat tines in an embodiment of the present disclosure.
Figure 10A:
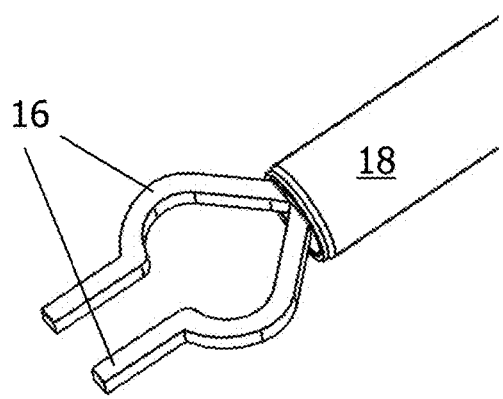
FIG. 10a shows forceps of a bipolar dissector with tines having curved portions and flat portions and a parallel tip section in an embodiment of the present disclosure.
Figure 10B:
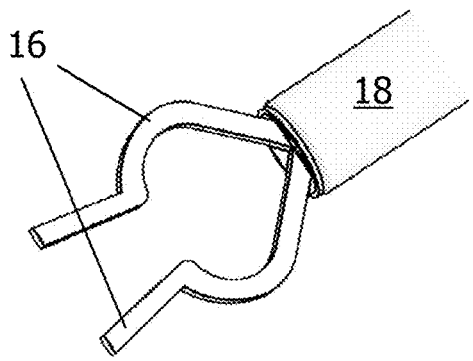
FIG. 10b shows forceps of a bipolar dissector with tines having curved portions and flat portions and a splayed tip in an embodiment of the present disclosure.

Referring to FIG. 8, a portion of the tines 16*a*/16*b* may be curved to angle away from the axis of the housing 18 and provide the contact surface for contacting the housing 18 to bring the distal tips of the forceps 16 together and may be curved to angle back toward the axis of the housing 18 toward the distal tips. Referring to FIG. 9, the tines 16*a*/16*b* may include angled flat, straight sections to angle away from the axis of the housing 18 and provide the contact surface for contacting the housing 18 to bring the distal tips of the forceps 16 together and may include another angled flat section to angle back toward the axis of the housing 18 toward the distal tips. Additionally or alternatively, the tines 16*a*/16*b* may cross over each other between the proximal end and the distal end, as shown in FIG. 9. Referring to FIG. 10*a* and FIG. 10*b*, a portion of the tines 16*a*/16*b* may be angled and flat to provide the contact surface for contacting the housing 18 and another portion of the tines 16*a*/16*b* may be curved to bring the distal tips of the forceps 16 together.

The distal portions of the tines 16*a*/16*b* in FIG. 8, FIG. 9, FIG. 10*a*, and FIG. 10*b* are flat. The distal portions of the tines 16*a*/16*b* in FIG. 8, FIG. 9, and FIG. 10*a* are parallel in the retracted states and come together to contact at their distal tips for gripping and pulling upon actuation. The distal portions of the tines 16*a*/16*b* in FIG. 10*b* are splayed in the retracted state and come together substantially parallel to each other upon actuation to provide a greater area of contact between the tines 16*a*/16*b* for gripping and pulling upon actuation.

Figure 11:
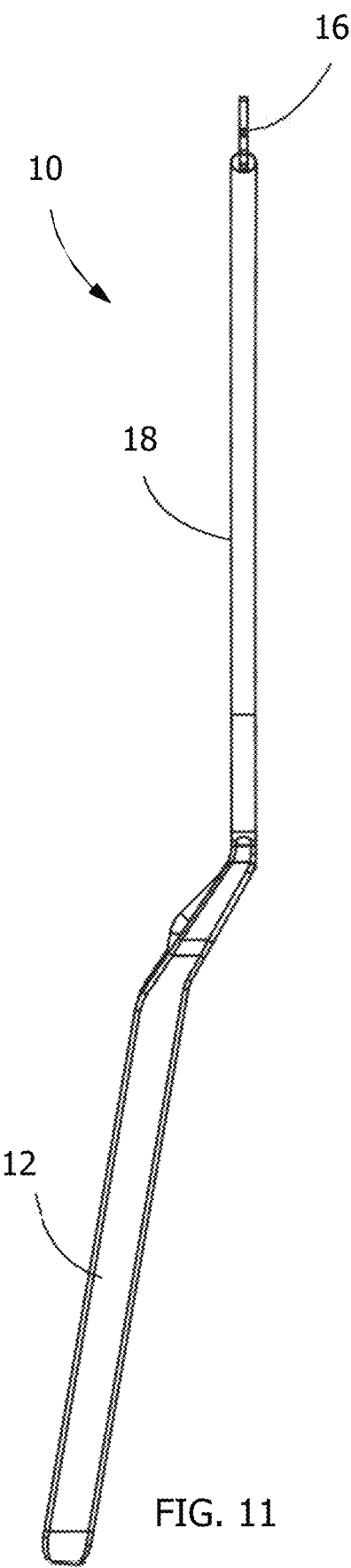
FIG. 11 shows a side view of a bipolar dissector with an angled offset handle in an embodiment of the present disclosure.

Alternatively to the offset of the handle 12 shown in FIG. 1 to FIG. 7, the handle 12 may be offset from the forceps 16 in other manners. Referring to FIG. 11, the handle 12 may be in a plane that is offset and at an angle to the plane of the forceps 16 rather than being offset and in a plane parallel to the plane of the forceps 16.

Figure 12:
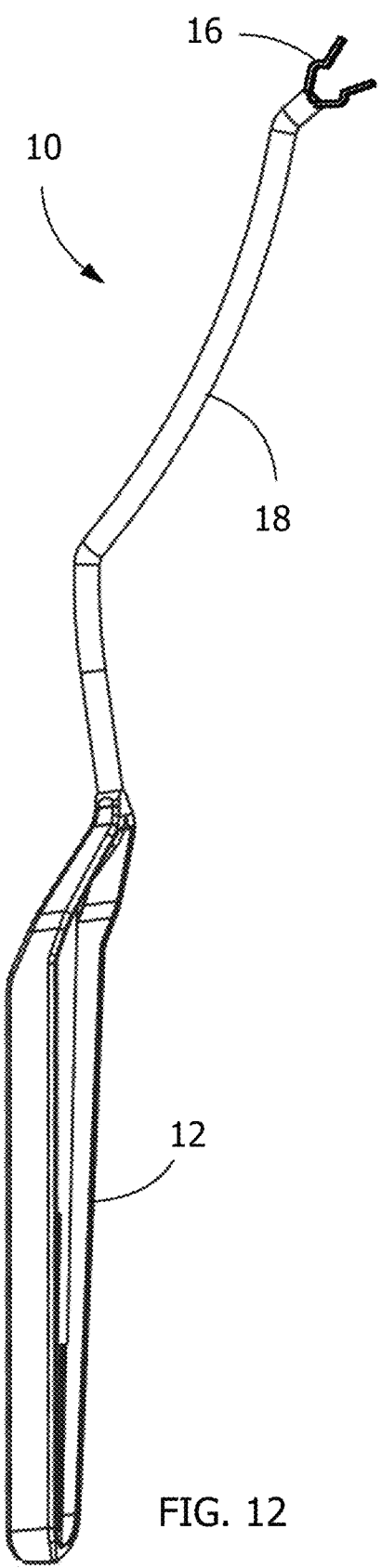
FIG. 12 shows a lowered side view of a bipolar dissector with a non-straight housing in an embodiment of the present disclosure.
Figure 13:
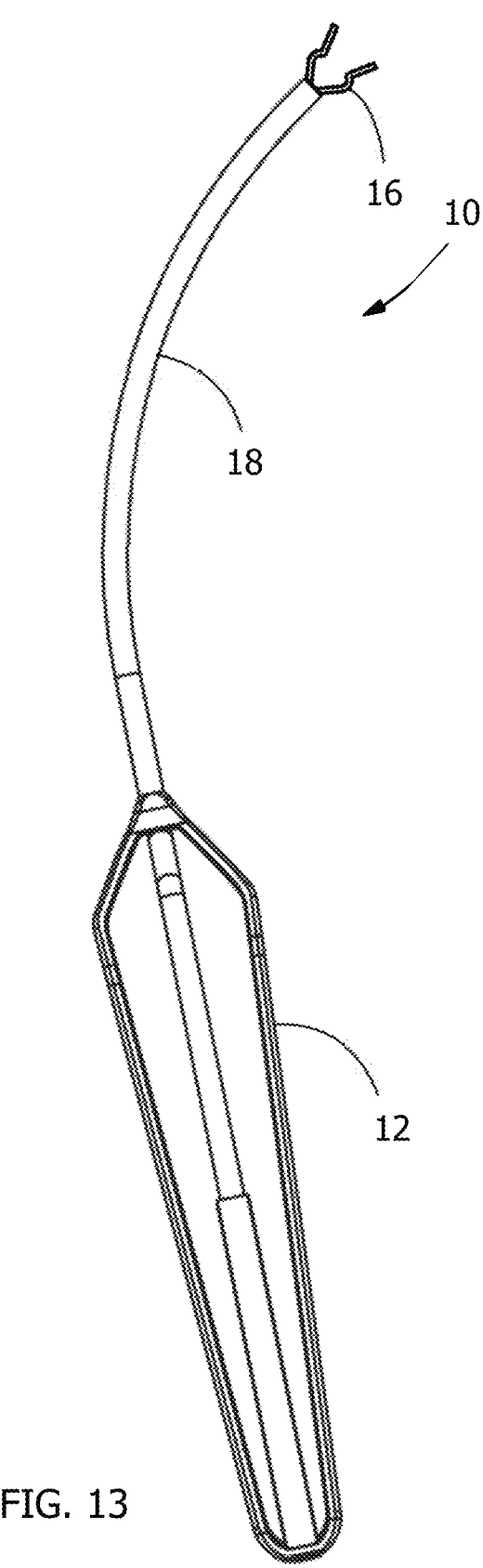
FIG. 13 shows a top view of a bipolar dissector with the housing curved in the plane of the forceps in an embodiment of the present disclosure.
Figure 14:
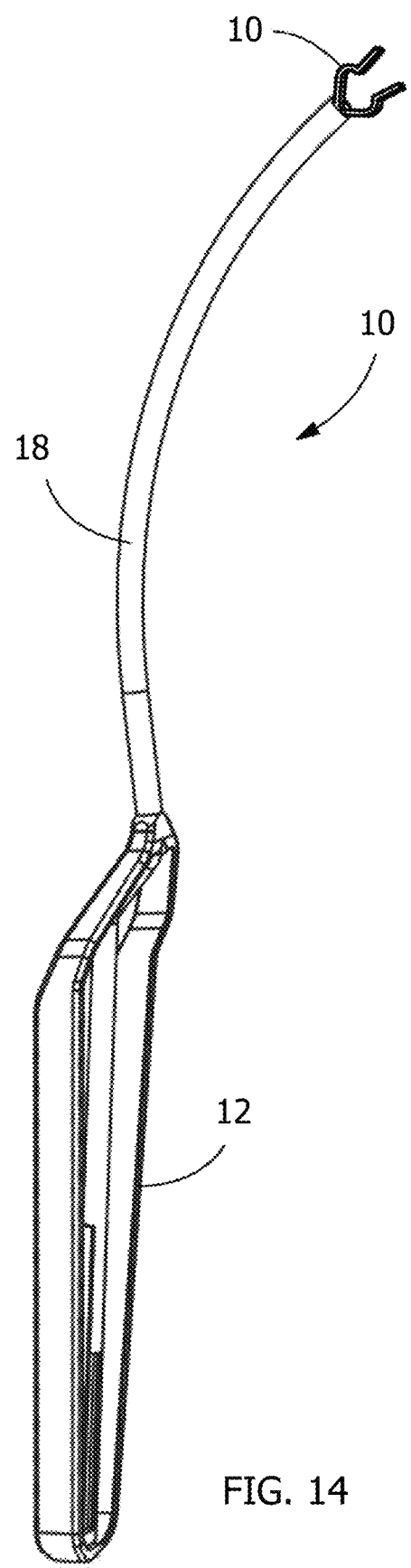
FIG. 14 shows a lowered side view of a bipolar dissector with the housing curved in a plane perpendicular to the plane of the handle in an embodiment of the present disclosure.

Alternatively to the housing 18 and the shaft 12 under the housing 18 being cylindrical as shown in FIG. 1 to FIG. 7, the axis of the housing 18 may be curved or otherwise not straight. In such embodiments, the shaft 12 may be flexible under a rigid housing 18 to conform to the contour of the housing 18 during activation and retraction. Alternatively, the housing 18 may be flexible over a rigid shaft 12 to conform to the contour of the shaft 12 during activation and retraction. Referring to FIG. 12, the housing 18 has an irregular contour in extending from the handle 12. Referring to FIG. 13, the housing 18 has a curved contour in extending from the housing 18, where the curve is in the plane of the forceps 16. Referring to FIG. 14, the housing 18 has a curved contour in extending from the housing 18, where the curve is in the plane perpendicular to the plane of the handle 12.

Embodiments of the present invention are not in any way limited in use for any particular type of surgery, and thus, may be use in spinal surgery in any mode of access, including, but not limited to direct surgical approaches, and minimally invasive approaches including direct, oblique or posterior-lateral, anterior (ALIF), posterior (PLIF), transverse (TLIF), lateral, and extreme lateral (XLIF), as well as in any other surgeries in the body, including within the brain, the bone extremities, and in the pelvis and abdomen.

As used herein, the singular forms "a", "an", and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

With respect to any references herein that may be made relative to a human patient, the terms "cephalad", "cranial", and "superior" indicate a direction toward the head, and the terms "caudad" and "inferior" indicate a direction toward the feet. Likewise the terms "dorsal" and "posterior" indicate a direction toward the back, and the terms "ventral" and "anterior" indicate a direction toward the front. And the term "lateral" indicates a direction toward a side of the patient, the term "medial" indicates a direction toward the mid line of the patient, and away from the side, the term "ipsilateral" indicates a direction toward a side that is proximal to the operator or the object being referenced, and the term "contralateral" indicates a direction toward a side that is distal to the operator or the object being referenced. More generally, all terms providing spatial references to anatomical features shall have meaning that is customary in the art.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

References to visualization using radiography as described in the exemplary techniques herein are merely representative of the options for the operator to visualize the surgical field and the patient in one of many available modalities. It will be understood by one of ordinary skill in the art that alternate devices and alternate modalities of visualization may be employed depending on the availability in the operating room, the preferences of the operator and other factors relating to exposure limits. While confirmation of instrument placement in the course of the technique is appropriate, the frequency and timing relative to the sequence of steps in the technique may be varied and the description herein is not intended to be limiting. Accordingly, more or fewer images, from more or fewer perspectives, may be collected.

One of ordinary skill will appreciate that references to positions in the body are merely representative for a particular surgical approach, and according to the exemplary embodiments herein, are suitable for any number of animal patients, including humans and other species. Of course, the type of surgery, target tissue, and species of patient may be different than is disclosed in the exemplary embodiments described herein. Further, all references herein are made in the context of the representative images shown in the drawings. Fewer or additional generic instruments may be used according to the preference of the operator. Moreover, references herein to specific instruments are not intended to be limiting in terms of the options for use of other instruments where generic options are available, or according to the preference of the operator.

Thus, while the disclosed embodiments have been described and depicted in the drawings in the context of the human spine, it should be understood by one of ordinary skill that all or various aspects of the embodiments hereof may be used in connection with other species and within any species on other parts of the body where deep access within the tissue is desirable.

Further, while various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts and features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated.

Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A bipolar dissector comprising:
    a handle includes a proximal end and a distal end, wherein the handle is actuatable by squeezing;
    a housing extending from and coupled to the distal end of the handle;
    a shaft coupled to the proximal end of the handle and extending past the distal end of the handle and through the housing to a distal end of the housing, the shaft comprising:
        a first electrical line extending from a proximal end of the shaft to a distal end of the shaft;
        a second electrical line extending from a proximal end of the shaft to a distal end of the shaft; and an insulating material electrically insulating the first electrical line and the second electrical line from each other and from the handle and the housing; and a pair of forceps comprising a first tine and a second tine, the first tine extending from the first electrical line at the distal end of the shaft at the distal end of the housing and the second tine extending from the second electrical line at the distal end of the shaft at the distal end of the housing;

wherein squeezing the handle, while coupled to the shaft at the proximal end, causes the handle to elastically deform to extend at the distal end towards the pair of forceps and push the housing axially with respect to the shaft towards the pair of forceps.

2. The bipolar dissector of claim 1, wherein the handle is offset from an axis of the housing.

3. The bipolar dissector of claim 1, further comprising electrical leads electrically coupled to the first electrical line and the second electrical line at the proximal end of the shaft and couplable to an electricity source.

4. The bipolar dissector of claim 1, wherein the shaft further comprises a fluid channel extending from a proximal end of the shaft to the distal end of the shaft.

5. The bipolar dissector of claim 1, wherein the handle comprises a pair of arms elastically squeezable to actuate the forceps.

6. The bipolar dissector of claim 1, wherein the distal end of the housing extends axially toward the forceps upon actuation of the handle and pushes on the forceps to cause distal tips of the forceps toward each other.

7. The bipolar dissector of claim 6, wherein the distal tips are straight and splayed in a retracted state.

8. The bipolar dissector of claim 6, wherein the distal tips are straight and parallel to each other in a retracted state.

9. The bipolar dissector of claim 1, wherein the first tine and the second tine each comprise a curved surface contacted by the housing upon actuation of the handle.

10. The bipolar dissector of claim 1, wherein the first tine and the second tine each comprise a flat surface contacted by the housing upon actuation of the handle.

11. The bipolar dissector of claim 1, wherein the housing is cylindrical.

12. The bipolar dissector of claim 1, wherein an axis of the housing is curved in a plane of the forceps.

13. The bipolar dissector of claim 1, wherein an axis of the housing is curved in a plane perpendicular to a plane of the handle.

14. The bipolar dissector of claim 1, wherein the housing is not straight in extending from the handle.

15. The bipolar dissector of claim 1, wherein the shaft is a tubular member that extends from the proximal end of the handle to the distal end of the handle and extends through the housing to the distal end of the housing.

16. A method of electrosurgery comprising:

placing a pair of forceps of a bipolar dissector at an electrosurgical site, the bipolar dissector comprising:

a handle includes a proximal end and a distal end;

a housing extending from and coupled to the distal end of the handle;

a shaft coupled to the proximal end of the handle and extending past the distal end of the handle and through the housing to a distal end of the housing, the shaft comprising:

a first electrical line extending from a proximal end of the shaft to a distal end of the shaft;

a second electrical line extending from a proximal end of the shaft to a distal end of the shaft; and an insulating material electrically insulating the first electrical line and the second electrical line from each other and from the handle and the housing; and the pair of forceps comprising a first tine and a second tine, the first tine extending from the first electrical line at the distal end of the shaft at the distal end of the housing and the second tine extending from the second electrical line at the distal end of the shaft at the distal end of the housing; and squeezing the handle to actuate the forceps;

wherein squeezing the handle, while coupled to the shaft at the proximal end, causes the handle to elastically deform to extend at the distal end towards the pair of forceps and push the housing axially with respect to the shaft towards the pair of forceps.

17. The method of claim 16, further comprising applying suction to the electrosurgical site by way of a fluid channel through the shaft of the bipolar dissector.

18. The method of claim 16, further comprising providing irrigation to the electrosurgical site by way of a fluid channel through the shaft of the bipolar dissector.

19. The method of claim 16, wherein the squeezing further comprises grabbing and pulling tissue at the electrosurgical site with the forceps.

20. The method of claim 16, further comprising supplying an electrical current to the forceps by way of the first electrical line and the second electrical line.

* * * * *